(12) United States Patent
Lavi et al.

(10) Patent No.: US 8,858,508 B2
(45) Date of Patent: *Oct. 14, 2014

(54) SYRINGE WITH AUTOMATICALLY TRIGGERED SAFETY SLEEVE

(75) Inventors: Gilad Lavi, Rishon Letzion (IL); Izrail Tsals, Newtown, PA (US)

(73) Assignee: West Pharmaceuticals Services of Delaware, Inc., Wilmington, DE (US)

( * ) Notice: Subject to any disclaimer, the term of this patent is extended or adjusted under 35 U.S.C. 154(b) by 1990 days.

This patent is subject to a terminal disclaimer.

(21) Appl. No.: 10/566,226

(22) PCT Filed: Jul. 28, 2004

(86) PCT No.: PCT/IB2004/051319
§ 371 (c)(1),
(2), (4) Date: Jan. 27, 2006

(87) PCT Pub. No.: WO2005/009519
PCT Pub. Date: Feb. 3, 2005

(65) Prior Publication Data
US 2006/0229569 A1    Oct. 12, 2006

Related U.S. Application Data

(60) Provisional application No. 60/491,196, filed on Jul. 31, 2003, provisional application No. 60/519,724, filed on Nov. 14, 2003.

(51) Int. Cl.
*A61M 5/32* (2006.01)
*A61M 5/31* (2006.01)

(52) U.S. Cl.
CPC ......... *A61M 5/326* (2013.01); *A61M 2205/581* (2013.01); *A61M 5/3271* (2013.01); *A61M 2005/3247* (2013.01); *A61M 5/3202* (2013.01); *A61M 2005/3109* (2013.01); *A61M 2205/582* (2013.01)
USPC ........................... 604/198; 604/192; 604/110

(58) Field of Classification Search
CPC ... A61M 5/32; A61M 5/3205; A61M 5/3243; A61M 5/3257; A61M 5/326; A61M 2005/3261; A61M 2005/3267
USPC ......... 604/192, 195, 196, 197, 198, 187, 181, 604/110
See application file for complete search history.

(56) References Cited

U.S. PATENT DOCUMENTS

| 2,752,918 | A | 7/1956 | Uytenbogaart |
| 3,811,441 | A | 5/1974 | Sarnoff |

(Continued)

FOREIGN PATENT DOCUMENTS

| DE | 3715337 A1 | 11/1988 |
| DE | 4120267 A1 | 12/1992 |

(Continued)

*Primary Examiner* — Laura Bouchelle
(74) *Attorney, Agent, or Firm* — Panitch Schwarze Belisario & Nadel LLP

(57) ABSTRACT

A medical injection device is provided which includes a shield system and a syringe. The shield system includes a housing, a shield telescopically received in the housing and slidably coupled to the housing and a driver that pushes the syringe stopper to cause drug injection. The driver is equipped with sensing elements that automatically detect empty syringe. A spring resiliently urges the shield from a retracted position to an extended position shielding the needle. The syringe is coupled to the housing. The shield is positioned externally to the syringe and the driver. The shield includes flexible latches to keep its position relative to the housing during storage and use. The axial movement of the driver in respect to the syringe causes an automatic release of the spring by sensors when the syringe is empty, allowing the spring to move and lock the shield in the extended position after use.

16 Claims, 17 Drawing Sheets

(56) References Cited

U.S. PATENT DOCUMENTS

| | | |
|---|---|---|
| 4,031,893 A | 6/1977 | Kaplan et al. |
| 4,378,015 A | 3/1983 | Wardlaw |
| 4,445,510 A | 5/1984 | Rigby |
| 4,553,962 A | 11/1985 | Brunet |
| 4,689,042 A | 8/1987 | Sarnoff et al. |
| 4,738,660 A | 4/1988 | Lucas |
| 4,755,169 A | 7/1988 | Sarnoff et al. |
| 4,838,857 A | 6/1989 | Strowe et al. |
| 4,923,447 A | 5/1990 | Morgan |
| 4,927,414 A | 5/1990 | Kulli |
| 4,941,880 A | 7/1990 | Burns |
| 4,969,874 A | 11/1990 | Michel et al. |
| 5,024,656 A | 6/1991 | Gasaway et al. |
| 5,092,842 A | 3/1992 | Bechtold et al. |
| 5,114,406 A | 5/1992 | Gabriel et al. |
| 5,137,511 A | 8/1992 | Reynolds |
| 5,201,708 A | 4/1993 | Martin |
| 5,244,465 A | 9/1993 | Michel |
| 5,267,963 A | 12/1993 | Bachynsky |
| 5,281,198 A | 1/1994 | Haber et al. |
| 5,295,965 A | 3/1994 | Wilmot |
| 5,300,030 A | 4/1994 | Crossman et al. |
| 5,342,320 A * | 8/1994 | Cameron ............ 604/192 |
| 5,360,410 A | 11/1994 | Wacks |
| 5,478,316 A | 12/1995 | Bitdinger et al. |
| 5,514,097 A | 5/1996 | Knauer |
| 5,599,309 A | 2/1997 | Marshall et al. |
| 5,637,094 A | 6/1997 | Stewart, Jr. et al. |
| 5,658,259 A | 8/1997 | Pearson et al. |
| 5,681,291 A | 10/1997 | Galli |
| 5,681,292 A | 10/1997 | Tober et al. |
| 5,779,677 A | 7/1998 | Frezza |
| 6,099,503 A | 8/2000 | Stradella |
| 6,159,181 A | 12/2000 | Crossman et al. |
| 6,280,421 B1 | 8/2001 | Kirchhofer et al. |
| 6,319,233 B1 * | 11/2001 | Jansen et al. ............ 604/192 |
| 6,319,234 B1 | 11/2001 | Restelli et al. |
| 6,419,658 B1 | 7/2002 | Restelli et al. |
| 6,544,234 B1 | 4/2003 | Gabriel |
| 6,569,123 B2 * | 5/2003 | Alchas et al. ............ 604/192 |
| 6,620,137 B2 | 9/2003 | Kirchhofer et al. |
| 6,743,203 B1 | 6/2004 | Pickhard |
| 2001/0005781 A1 | 6/2001 | Bergens et al. |
| 2002/0193746 A1 * | 12/2002 | Chevallier ............ 604/197 |
| 2003/0093036 A1 | 5/2003 | Crossman et al. |
| 2003/0105430 A1 | 6/2003 | Lavi et al. |
| 2003/0229314 A1 * | 12/2003 | McWethy et al. ............ 604/197 |

FOREIGN PATENT DOCUMENTS

| | | | |
|---|---|---|---|
| EP | 0186916 B1 | 12/1988 | |
| EP | 0516473 A1 | 12/1992 | |
| EP | 0518416 A1 | 12/1992 | |
| EP | 0666084 | 8/1995 | |
| FR | 986154 | 7/1951 | |
| FR | 2506151 | 11/1982 | |
| FR | 2616221 * | 6/1987 | ............ A61M 5/20 |
| FR | 2616221 | 12/1988 | |
| FR | 2770404 | 5/1999 | |
| WO | 94/28964 | 12/1994 | |
| WO | 99/33504 | 7/1999 | |
| WO | 0050107 | 8/2000 | |
| WO | 00/62839 | 10/2000 | |

\* cited by examiner

SYRINGE WITH AUTOMATICALLY TRIGGERED SAFETY SLEEVE

BACKGROUND OF THE INVENTION

1. Field of the Invention

The field of the invention relates to syringe safety systems and in particular to syringe shield systems for protecting against needle sticks.

2. Brief Description of the Related Art

Syringes are well known medical devices for administering medicaments, drugs and vaccines to patients. Prefilled syringes are generally considered as those which are filled with a selected dosage of medicament, drug or vaccine by a pharmaceutical manufacturer for distribution to the end user. They are generally comprised of a glass barrel which contains the medicament, drug or vaccine, and a stopper slidably mounted within the barrel. The distal end of the barrel includes a needle cannula or the like affixed thereto or a connector for a needle cannula assembly such as a Luer connector. The proximal end of the syringe includes an integral flange and is open to allow the insertion of a stopper and a plunger assembly. The plunger and stopper assembly allows the user to apply manual force to the plunger, causing the medicament, drug or vaccine to be delivered through the needle cannula or other piercing element. The healthcare worker or patient grips the flange and applies pressure to the plunger generally with the thumb.

The use of a sharp-pointed piercing element entails several types of risks. As long as the syringe is not in use ifs content is protected by a sterility cover that also prevents accidental an needle prick. Once the needle is exposed there are risks of accidental needle prick after use when the needle is contaminated, of accidental needle prick in case the syringe was not properly disposed of, and a risk of accidental or deliberate re-use. To avoid such accidents, many prior art hypodermic syringes have included different safety shields. Some of these considered telescopic shielding over the syringe barrel, others consider unique glass barrels. Telescoped shields can be moved between a retracted position, where the needle is exposed for use, to an extended position where the needle is surrounded by the shield.

U.S. Pat. No. 6,159,184 describes such a telescopic shield where the user is expected to identify the end of drug delivery and then use his second hand to manually push the shield until it locks to the holder. Sampson et al demonstrate this approach in a number of earlier patents such as U.S. Pat. No. 6,004,296, U.S. Pat. No. 4,425,120 and U.S. Pat. No. 4,573,976 also planned for a prefilled syringe.

U.S. Pat. No. 4,923,447 by Morgan discloses a shield system for hypodermic syringes which is spring-actuated. The release of the spring and triggering of the safety feature depends on the users action.

It is ordinarily desirable to lock the needle shields in the protected positions, and a number of prior art designs provide for such locking. Some systems, such as those disclosed in U.S. Pat. Nos. 5,201,708, 5,242,240 and U.S. Pat. No. 5,318,538 by Martin, are designed to allow the shields to be retracted from their locked, extended positions.

Another approach is demonstrated in U.S. Pat. No. 6,613,022 by Doyle where the user unsnaps a preloaded spring by moving the driver close to it's end of delivery position. The user is also expected to release his gripping fingers to allow the telescoping shield, which is external to the holder in that case, to slide forward and lock.

The safety shield could be activated by different means. In U.S. Pat. No. 6,613,022, the driver has to reach a certain position relative to the holder; in patent application 20030050607 by Gagnieux the user is expected to apply an increased pressure over the driver to do the same.

SUMMARY OF THE INVENTION

According to the present invention there is provided an injection device comprising:
- a housing having a proximate end and a distal end, the distal end having an opening therein;
- a cartridge barrel within the housing, the cartridge barrel having proximate and distal ends;
- a needle cannula fixed to the distal end of the cartridge barrel, or attachment means for fixing a needle cannula to the distal end;
- a stopper within the cartridge barrel;
- a driver coupled to the stopper;
- a shield coupled to the housing and slidable between a retracted and an extended position;
- shield driver means activateable to urge the shield from the withdrawn position to the extended position; and
- sensor means moveable with said driver and in slidable contact with an exterior surface of said cartridge barrel or an interior surface of said housing, the sensor means arranged to detect an end profile of the barrel or housing and to trigger activation of the shield driver means upon detection.

This invention relates to a safety shield system for a syringe, medical cartridge or the like and such a system as used in combination with an assembly capable of functioning as a syringe. In accordance with the preferred embodiment of the system, the user is able to use a prefilled syringe using a similar action to that used with simple prefilled syringes. The user is able to observe the drug, to purge air, to titrate the desired dose, to hold the syringe as he/she is trained, to penetrate the skin and inject. Shielding of the needle will occur automatically without any further step required from the user. The shielding will be synchronized with the reaching of the end of delivery or the emptying of the cartridge.

In accordance with the objects of the invention, a medical device is provided which includes an automatically operable shield system mounted to a syringe barrel. The system includes a tubular housing which defines an assembly enclosure. A tubular needle shield is slidably attached to the housing and preferably is telescopically received within the housing. The syringe barrel is received within the housing and shield assembly, partially within the tubular shield. The shield is extendable from a retracted position and encloses the needle cannula following the end of injection.

In the disclosed embodiment, the shield includes a stop member adjacent its proximal end and the housing includes a stop member adjacent its distal end which releaseably retains the shield in its retracted position. In the preferred embodiment, the stop members on the shield comprise two latches adjacent to slits in the housing. The stop members prevent the shield moving forward before the end of delivery is achieved. The strength of that connection should be sufficient to withstand the shield's weight and effects of impact only. There is no force applied on the stopping members. The force required by the spring to disengage the shield from the housing is minimal.

A compressed spring is trapped on the driver assembly. During injection the driver is moved forward by the user in order to push the drug from the glass barrel into the users tissue. The shield is releaseably retained in the housing. The spring is released from the driver and biases the shield axially toward the extended position following injection. Upon application of a force by the spring, the shield is released from the retracted position and covers the needle.

The driver includes a central plunger acting like a conventional rod and two side arms acting as sensing elements. The sensing elements are the deflectable arms trapping the spring. The sensing arms act like a cam, which under the spring's load, senses the syringe's external profile. When the cams reach the distal side of the barrel the arms deflect and the spring is released from the driver. The spring bypasses the driver, impacts the shield, and releases the latches. Once the shield is released the spring drives it to the extended position where it is locked.

The proximal end of the housing is preferably adapted to engage and retain the syringe flange upon receipt of the syringe barrel through the proximal end of the housing. Once the syringe is snapped to the housing it will remain stationary with respect to it.

Prefilled syringes are sometimes used to aspirate drug, for example to mix a second drug into a filled cartridge. For that purpose it is important to have an axial connection between the driver and the syringe stopper. The axial attachment is achieved by having either a snap or a thread; a female part in the rubber stopper and a matching male part on the distal end of the driver plunger. The disclosed embodiment shows a snap connection between the plunger and the stopper yet, as will be further explained, a threaded connection is applicable too.

When compared to other known techniques the current invention is unique by being the closest to regular manual injection. Therefore it is expected that it will take a shortest training for the user to get comfortable with using the system. The described embodiment does not require any additional actions from the user and is automatically triggered by the internal conditions of the system. The activation of the automatic safety feature is affected by a minimal chain of dimensions and is involving only a single part in addition to the syringe.

DETAILED DESCRIPTION OF THE INVENTION

Figure 1:
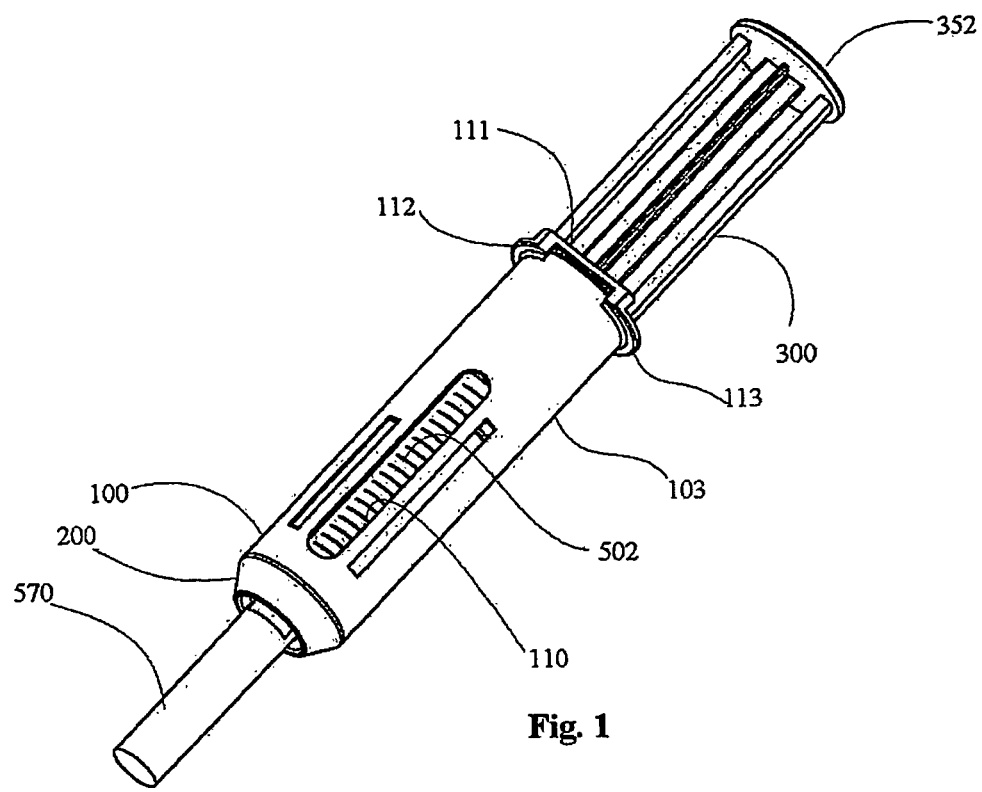
FIG. 1 is an isometric view of a preferred embodiment according to the invention.
Figure 1A:
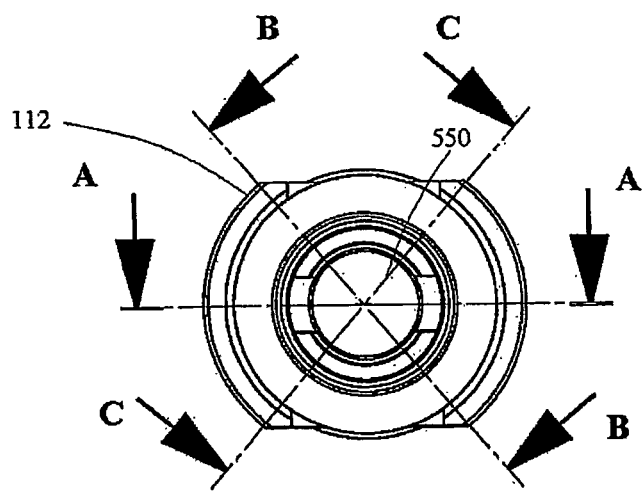
FIG. 1A defines the planes of the device cross sections as A-A, B-B, and C-C, where A-A is the cross section through the driver side arms providing the observation window perspective, B-B is a cross section through a plane of the discard latches and C-C is a cross-section through a plane of the discard stoppers.

A safety system is applied on a glass or plastic pre-filled syringe to protect users from any accidental needle prick after injection and/or to prevent reuse of a single use device. The accompanying figures clearly illustrate the three molded plastic parts which combine to form an embodiment and the pre-filled cartridge sub-assembly.

The following description considers three main stages in the use of the preferred embodiment: the storage condition of the assembled system; the end of delivery before removing the injection device from the tissue; and the system after removal from the injection site with the needle automatically shielded and secured.

The operation of the device described in the preferred embodiment follows the conventional way of using a simple standard pre-filled syringe. The syringe assembly (including prefilled syringe) is packaged to protect its content. Once the syringe is taken out of the packaging it is necessary to follow the manufacturers instruction: check the drug and its labeling, and identify the specific device details. In order to make that possible the safety device is fabricated using transparent polymers such as acrylic, polycarbonate or polystyrene. The selected materials do not require sterilization. The user should be able to purge the air bubble, titrate the required dose by using the syringe scale as it is currently done when using similar marketed products. In some specific cases the user will need to aspirate additional drug or diluent. The embodiment should consider this need by enabling a stopper motion in both proximate and distal directions through a reliable connection between the plunger and the stopper. The above activities will occur after the needle cover assembly is removed. The safety features should make it possible for the user to interact with the system in same way as with simple pre-filled syringes.

The injection process follows all commonly known methodology. The device should create minimal interference in any type of eye contact with the device that the user might need. There will be a certain increase in the typical device diameter since additional barriers are added to the cartridge. However that increase does not make any difference in the way of use.

Unlike other applications described in the background for this invention, this invention does not require any additional actions from the user. Injection process proceeds as usual. Once the end of injection is reached the shielding system is automatically triggered, providing the user a tactile indication of end of delivery in addition to the usual visual indication. As the user is removing the device from the injection site the shield is moved by a spring in the distal direction covering the needle. The shield is locked to the housing. The ejection of the shield by a spring does not require any increase in the force applied by the user for injection. The device needle is secured with the device ready for safe discard.

An basic operation principle used in the described embodiment is a sensing elements sliding over the external side of the cartridge and sensing the end of the barrel while automatically triggering the shielding system.

Figure 2:
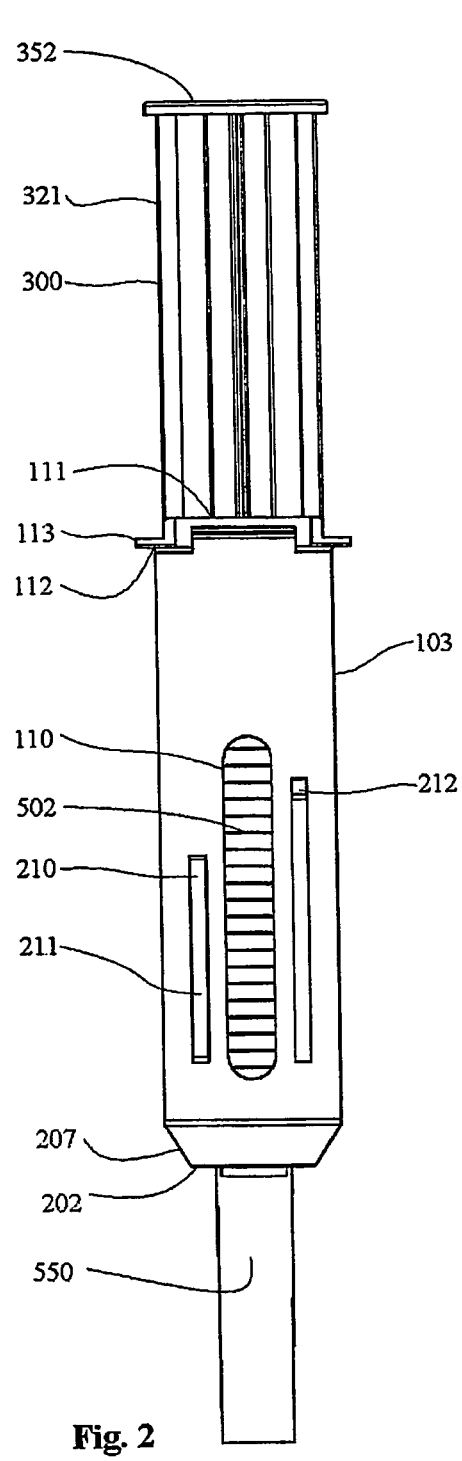
FIG. 2 is an external view of the device from the observation window perspective in a storage position.
Figure 3:
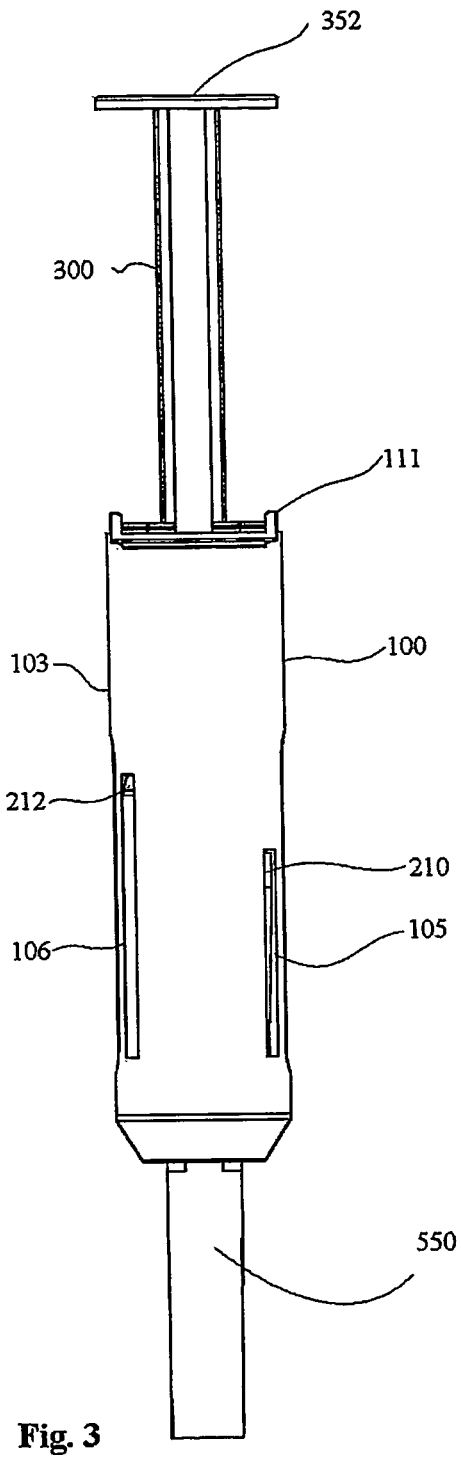
FIG. 3 is an external view of the device in a plane perpendicular to the plane in FIG. 2 in a storage position.

FIGS. 1 to 3 show different views of an embodiment of the invention in an initial unused state. These and other figures do not reflect the transparency of the plastic components. The safety syringe has a housing 100, a shield 200 and a driver 300. The spring 400 is positioned inside the assembly. It is important to position the spring where it will not interfere with viewing the scale and/or the drug. An observation window 110 (or a clear housing) is exposing the cartridge scale 502 and the drug 560. The user holds the housing 100 at the finger grips area 112 and applies force, usually by the thumb, over 352 part of the driver 300. The needle cover assembly 570 is removed prior to use. The needle cover assembly 570 exposed to the user is either a rigid plastic part 550 enclosing the elastomer sterility cover 540 or is the elastomer sterility cover 540 itself.

Figure 4:
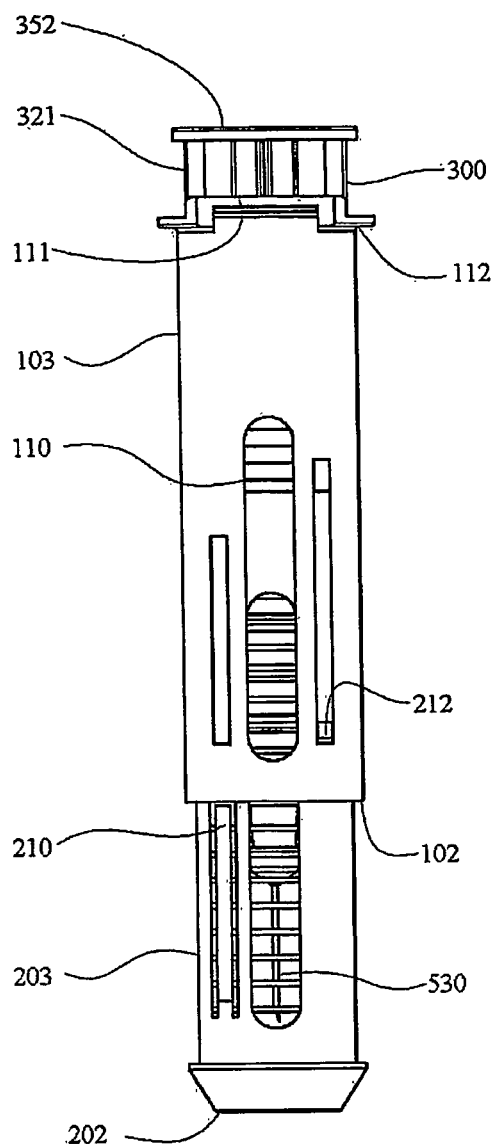
FIG. 4 is a view as in FIG. 2 with the device in a discard position.
Figure 5:
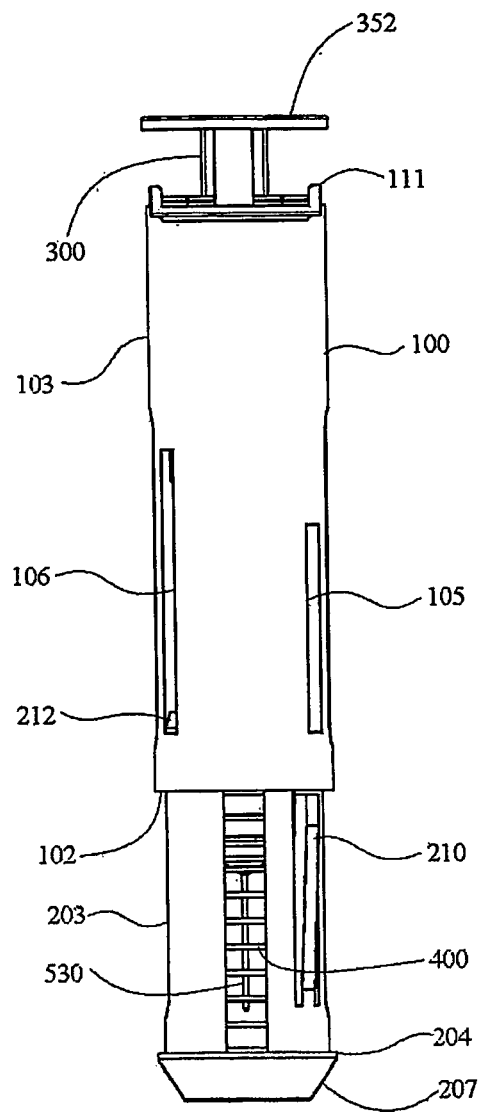
FIG. 5 is a view as in FIG. 3 with the device in a discard position.

FIG. 4 and FIG. 5 illustrates the device following use, and in particular following the activation of the shield. The shield discard stopper 212 has moved from the top of the guiding track 106 in FIG. 2 to the bottom of same track in FIG. 4 preventing further distal motion of the shield. Furthermore the discard latch has deflected outward and prevents the reverse motion of the shield 200 as illustrated in FIG. 4 and FIG. 5. The discard latch is initially positioned at the top of the guiding track 105.

Figure 6:
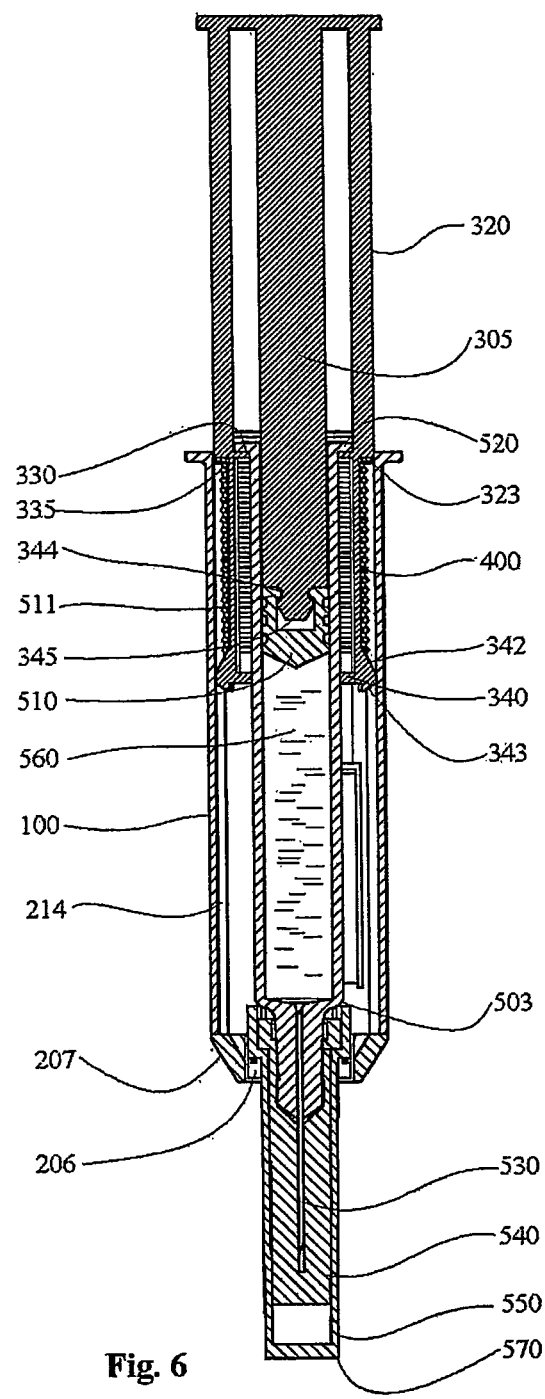
FIG. 6 is a cross-section view of the device in plane A-A per FIG. 1A when in a storage position.
Figure 7:
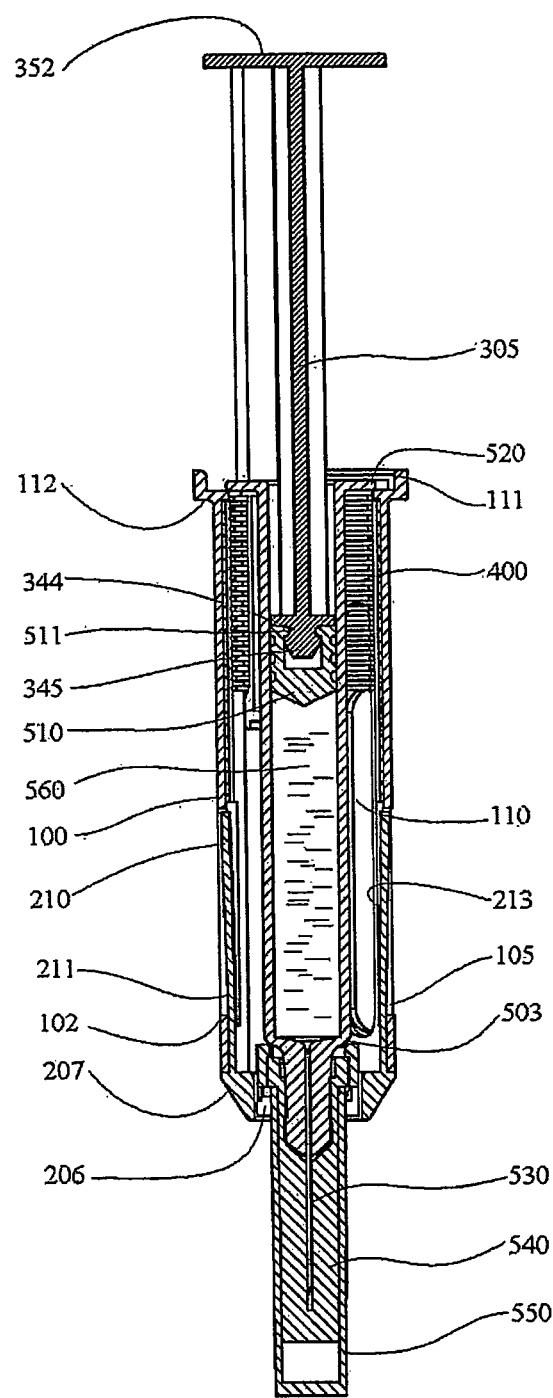
FIG. 7 is a cross-section view of the device in B-B plane per FIG. 1A when in a storage position.
Figure 8:
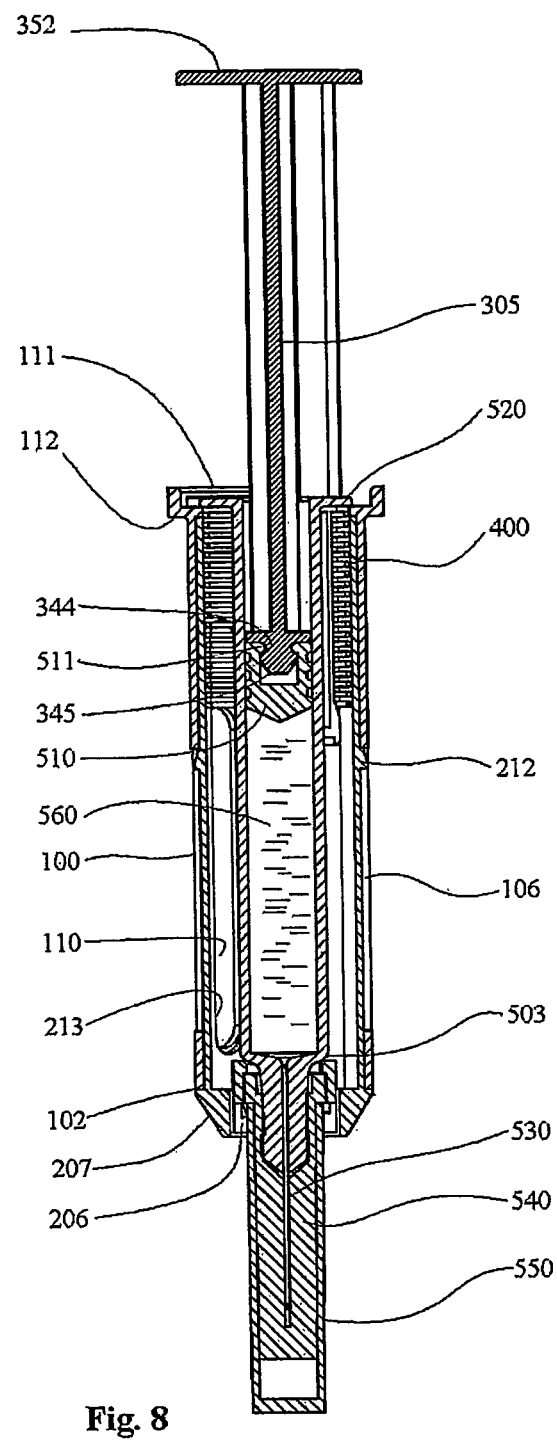
FIG. 8 is a cross-section view of the device in C-C plane per FIG. 1A when in a storage position.
Figure 9:
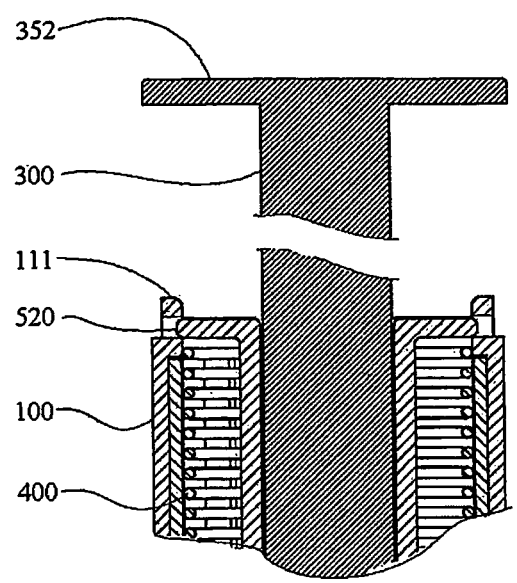
FIG. 9 is a close-up view of the cross section of the syringe flange and housing interface.
Figure 10:
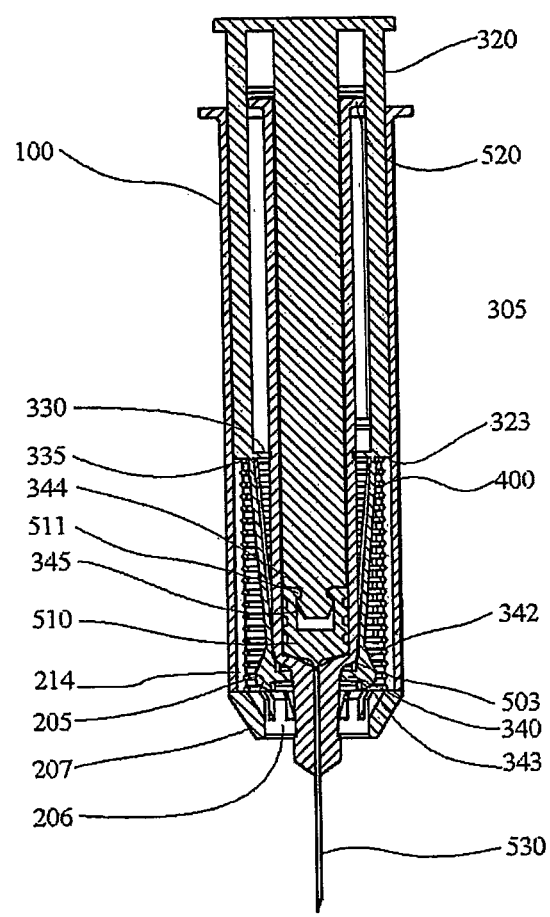
FIG. 10 is a cross-section view of FIG. 6 after delivery and before removal from injection site.
Figure 11:
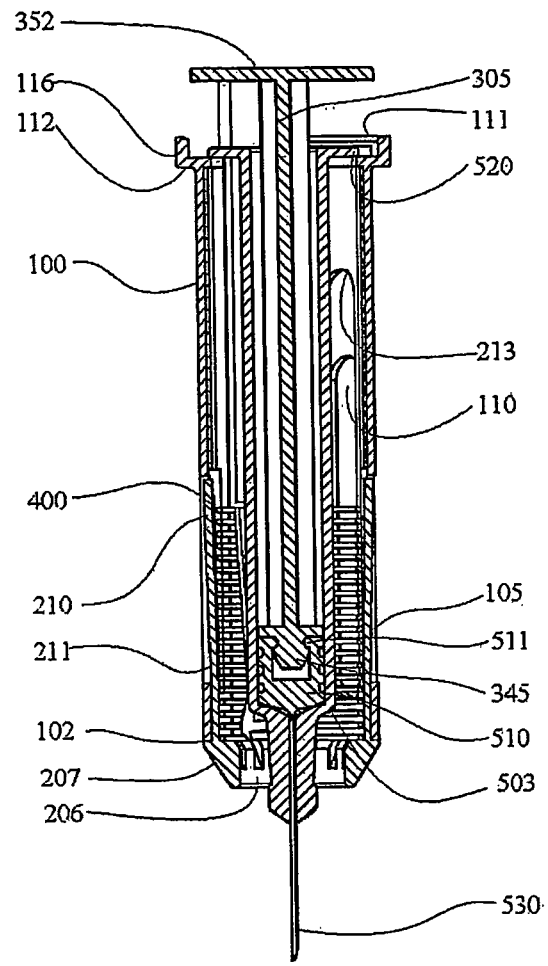
FIG. 11 is a cross-section of FIG. 7 after delivery and before removal from injection site.
Figure 12:
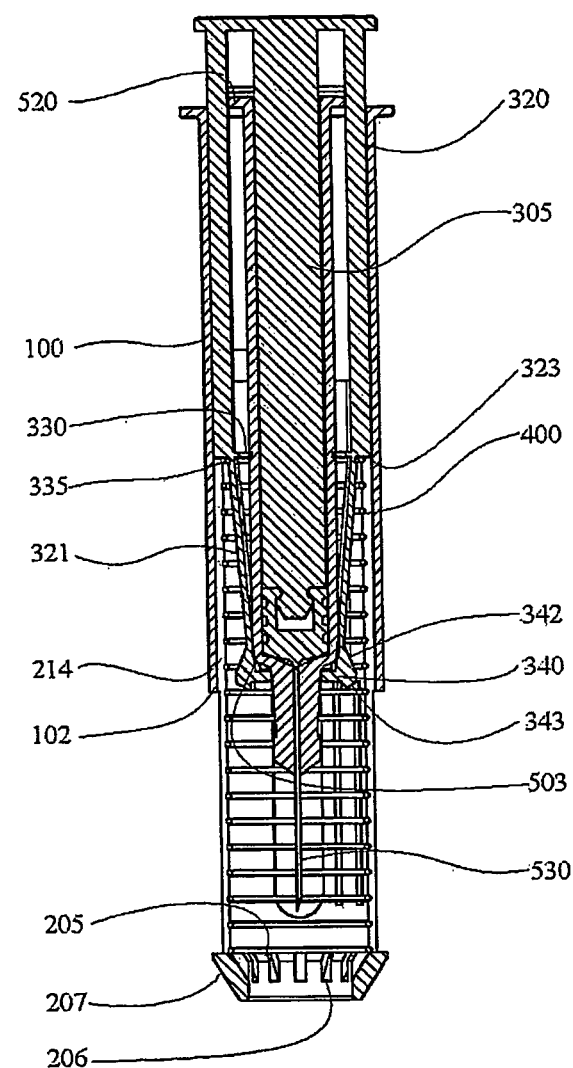
FIG. 12 is a cross-section of FIG. 6 with the device in the discard position after the removal from the injection site.
Figure 13:
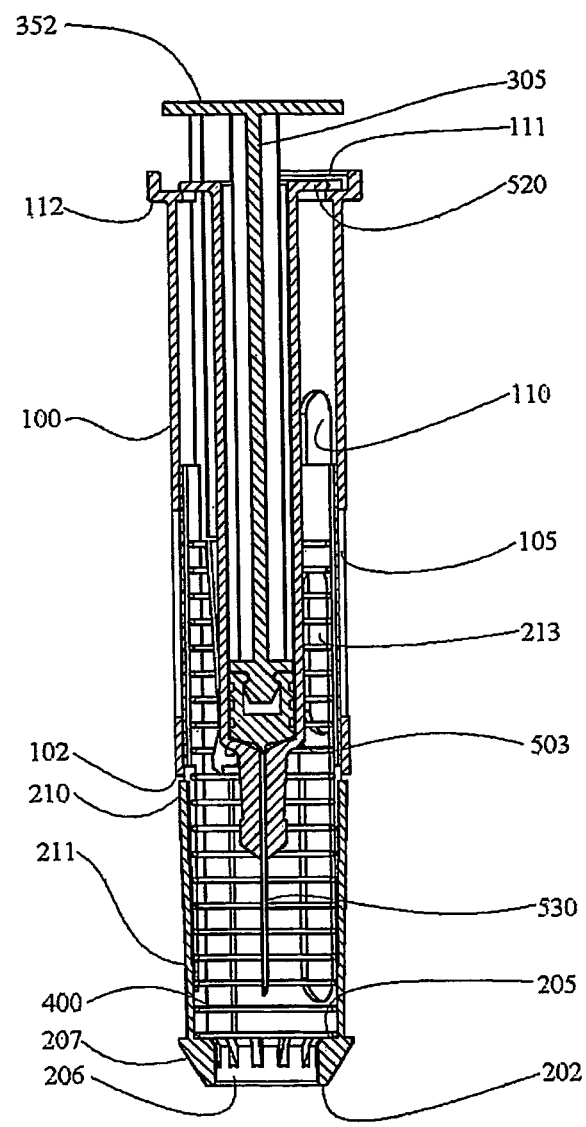
FIG. 13 is a cross-section of FIG. 7 with the device in the discard position after the removal from the injection site.
Figure 14:
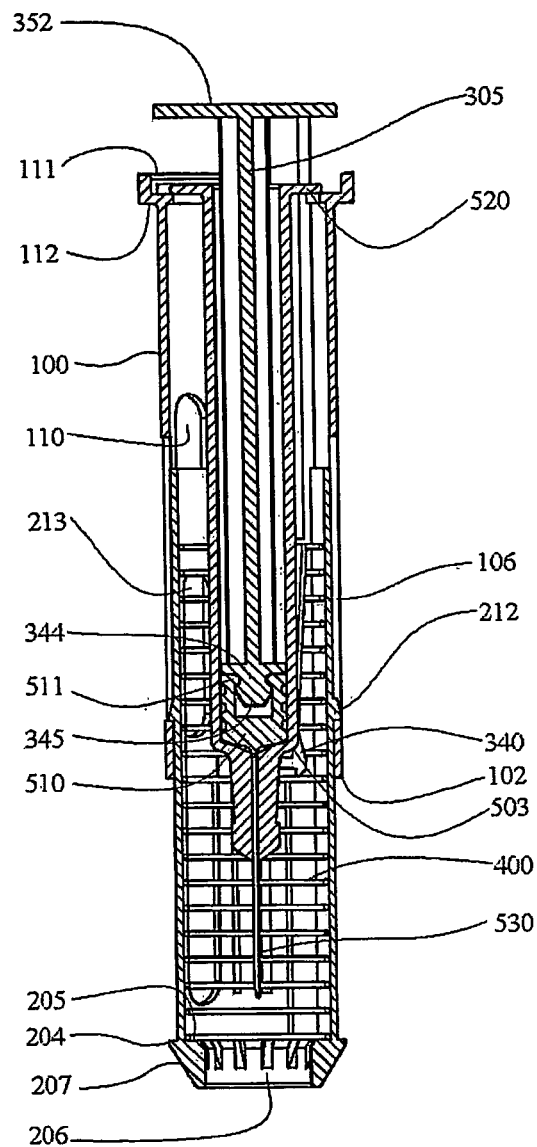
FIG. 14 is a cross-section of FIG. 8 with the device in the discard position after the removal from the injection site.

FIG. 6 through FIG. 14 show cross section views of the device describing 3 positions from 3 different perspectives. The A-A plane is parallel to the observation window 110 allowing a clear view of the driver 300 in different operation steps. FIGS. 6, 10 and 12 are all cross-sections in plane A-A. Cross section B-B is in a plane of the discard latch 210, allowing a clear view of latch 210 in slit 105 at different operation steps. FIGS. 7, 11 and 13 are all cross-sections in plane B-B. Cross section C-C is in a plane of stopper 212, allowing a clear view of the stopper 212 in slit 106 in different operation steps. FIGS. 8 and 14 are cross-sections in C-C plane.

FIG. 6, FIG. 7 and FIG. 8 illustrate different cross-section perspectives of the embodiment before use. The driver is unable to move to the distal side of the barrel since the cannula 530 is occluded by 540. The movement of the driver to the proximal side is also prevented by same means.

FIG. 9 is a close-up view showing flange 520 engaged to the housing 100 by snaps 111. Snaps 111 are preventing axial movement of the cartridge while housing slits 114 engaged with arms 320 prevent the driver rotational movement. Cartridge 500 is snapped to the housing by 111 and is supported in the radial plane by cams 340 pressed against the barrel 501 by the reaction of the spring 400. The removal of the sterility cover assembly 570 could be accomplished by pulling on 570. The cartridge is supported by the housing flange 116 when the needle cover assembly 570 is removed.

The use of the device starts with the removal of the needle cover assembly 570. After the air purge, titration and other steps are completed, the user starts the injection process by holding the device by the housing finger grip area 112 with two fingers and a thumb on the base/knob 350. The needle is inserted in a conventional way. Then the driver is pushed by the thumb while the safety syringe is held by two other fingers. The driver 300 moves forward while carrying the pre-loaded spring 400. With the exception of the axial displacement of the driver and stopper there are no changes in the relative positioning of other components in this embodiment.

End of delivery is detailed in FIG. 10 and FIG. 11. FIG. 10 shows the driver after cams 340 have run off the end of the barrel 503. The distal arm 322 of the driver 300 deflects under the spring 400 force to its molded state. Spring 400 will continue to slide along the cam cone 342 until it bypasses it. The proximal side of the spring is still pushing back the driver over spring support 323 while its distal side applies a force on the surface 205 of the shield flange 204. The user is not expected to perform any additional steps outside actions related to the common injection techniques. That spring impact additionally provides to the user both a tactile and audible indication of the end of delivery signaling time to remove the device from the injection site.

FIGS. 12, 13 and 14 show the preferred embodiment after the syringe assembly has been removed from the injection site and is ready for disposal. Under the axial force of spring 400 the shield 200 moves to the distal side and becomes locked. The forward motion of the shield 200 allows latches 210 to deflect out until these engage the distal edge 102 of the housing 100. During the forward motion of the shield 200, the spring proximal end is supported by spring support 323 of the driver 300. A potential reverse motion of the driver 300 is prevented by the support provided by cams 340 on the end 503 of the barrel 501. Stopper 212 (FIGS. 8 and 14) slides in slits 106 from its proximal end until the distal side, and prevents the removal of the shield 200 from the device. Injection is completed with the device secured for disposal.

After the device is used and the shield ejected by the spring, reuse is highly difficult to perform due to the position of spring 400 acting as a supporting cylinder inside tubular body 203.

Figure 15:
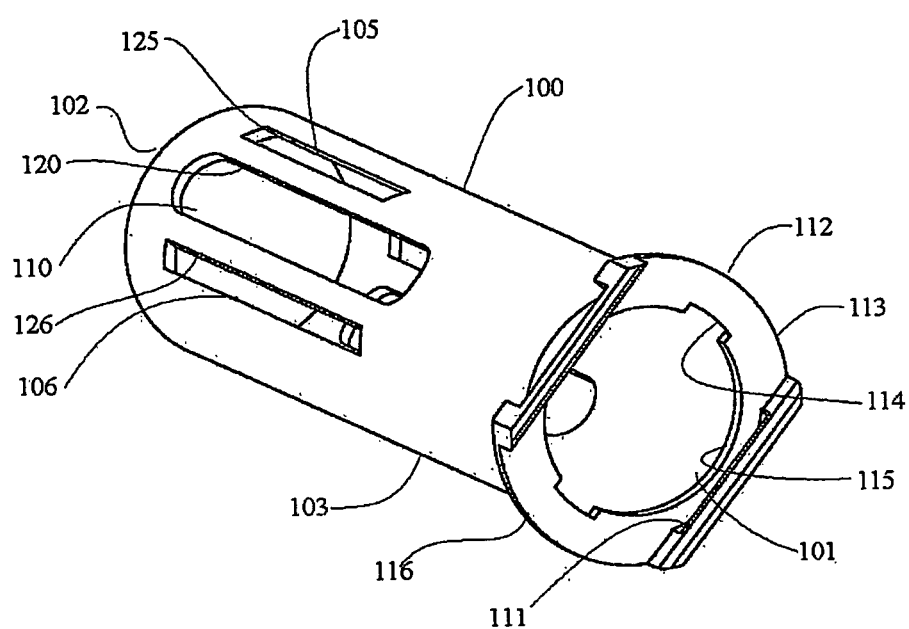
FIG. 15 Housing isometric view.

Individual component description:

The housing 100 is shown in FIG. 15. The housing 100 has a tubular section 103 and a flange 116 on its proximal side 101. The distal side 112 of the flange 116 is used for finger gripping. Different shapes of the gripping area could be used in the preferred safety syringe embodiment.

The proximal flange surface 113 of the housing flange 116 has locking elements 111 to permanently attach the cartridge flanges 520 (the cartridge is described in FIG. 19) to the housing 100 during assembly. Snaps 111 are dimensioned to capture the wider side of the cartridge flange. The cartridge 500 is stationary with respect to the housing during use.

The housing 100 has also three sets of longitudinal openings in its cylindrical section 103 including an observation window 110 on both sides of 103, a discard latch guiding track 105 and a stopper guiding track 106. Tracks 105 and 106 could be arranged across the diameter of 103. The tracks 105 and 106 and the observation windows 110 are coaxial with the axis of the housing. The side walls of 110, 105 and 106 could be parallel as illustrated in FIG. 15 to simplify the part manufacturing by injection molding. Furthermore, the observation window 110 is optional for clear plastic materials.

Flange 113 has a central opening with a diameter 115. The diameter 115 is above the external diameter of the spring 400 yet it is smaller than the diameter of the cartridge flange 520. Snaps 111 are arranged to lock the cartridge on its larger side 520 adjacent to the proximal surface of 113 of the housing flange 116. Flange 116 has two slits 114 to accommodate the driver side arms.

Figure 16:
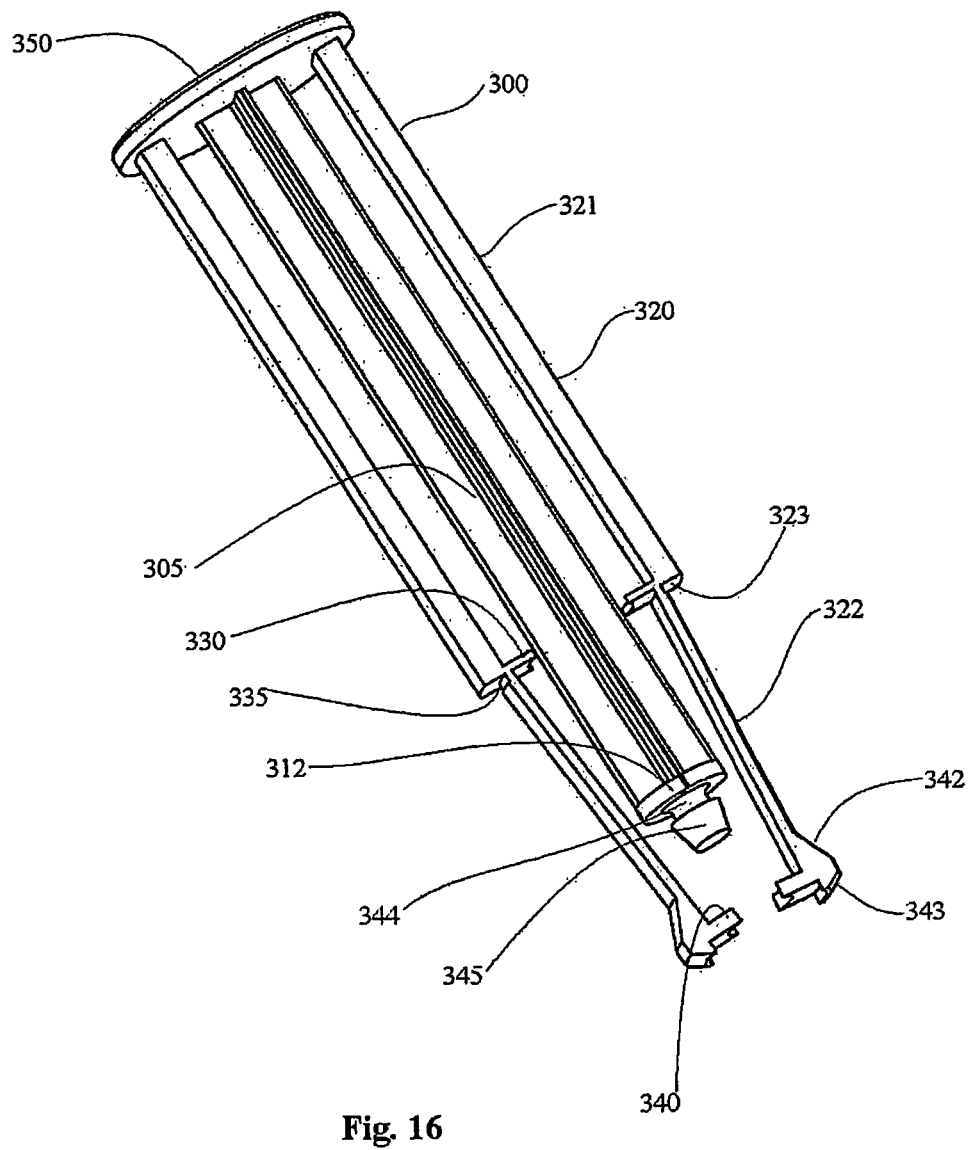
FIG. 16 Driver isometric view.

Driver 300 is detailed in FIG. 16. Driver 300 has a plunger 305 similar to a conventional syringe plunger. At the end of the plunger 305 is a knob 345 with a grove 344 and a plate 312 to capture the stopper. Alternatively the knob 345 could have a thread for connecting to the stopper of the cartridge.

On its proximal side the driver 300 has a base 350 acting as a conventional push pull knob. The base 350 also functions as a bridging element with the plunger 305 and side arms 320 attached to it. Each side arm 320 has a front arm section 322 and a rear arm section 321. The middle point where 321 turns into 322 has a protrusion 330. The protrusion 330 contacts and slides on the surface of the cartridge barrel.

The front arm section 322 is designed to trap and retain a preloaded spring while the device is in storage. The proximal end of the spring rests on a spring support 323. The distal end of the spring releasably rests on a cam cone 342. The distal end of the front arm section 322 further has a cam 340 resting on the cartridge barrel and a front taper 343 to assist in the assembly. 342 is able to allow the bypassing of the spring after end of delivery is sensed. The cam 340 follows the external shape of the cartridge and acts as the system sensor. Front arm 322 could have a reduced thickness 335 on its proximal end performing the function of an axis.

Figure 17:
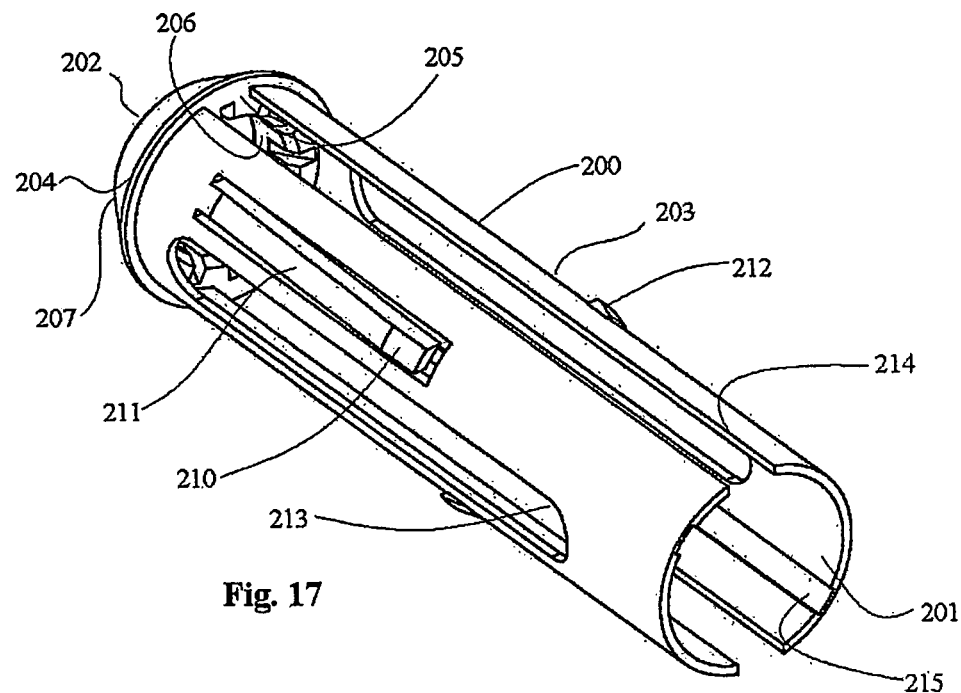
FIG. 17 Shield isometric view.
Figure 18:
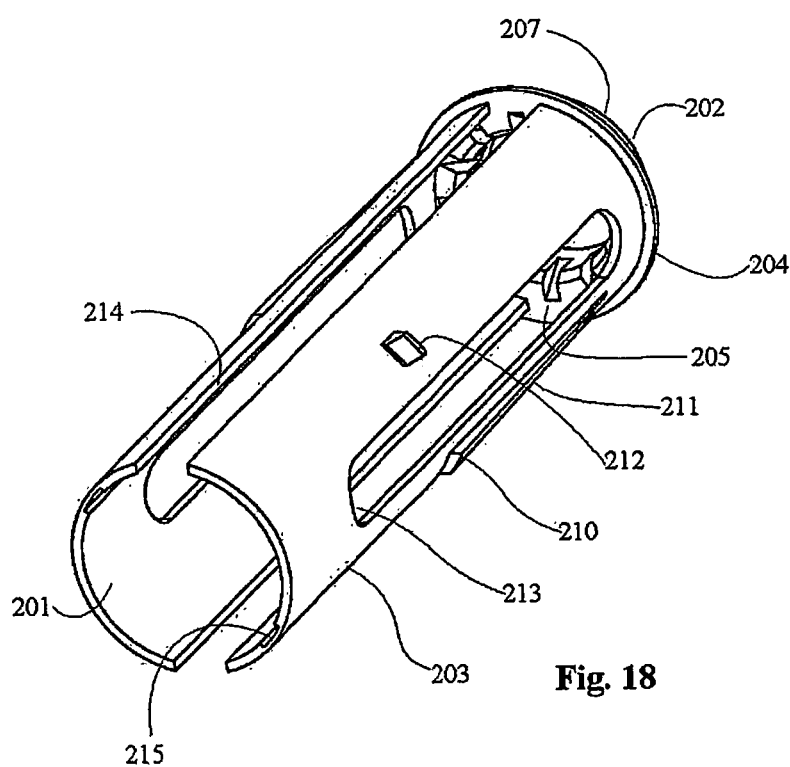
FIG. 18 Shield isometric view facing window.

Shield 200 is detailed in FIG. 17 and FIG. 18. The shield 200 has a tubular body 203. The shield 200 has a proximal end 201 and a distal end 202. It also has a flange 204 on the distal end 202 of the tubular body 203. The external diameter of 203 is in a sliding relationship with the inner diameter of the tubular section 103 of the housing. The flange 204 has a needle opening 206 with a diameter big enough to allow the removal of the needle cover assembly 570. The proximal side 205 of the flange 204 is flat while its external side 207 of the flange 204 could be shaped like a cone for better needle visibility. Tubular section 203 could have two openings 213 positioned across the diameter and matching housing windows 110 to create the safety syringe observation window. The longitudinal slits 214 act as the driver side arm guiding tracks. Undercuts 215 are introduced to assist in the molding of discard latches 210. Discard latches 210 provide two functions: first to keep the shield in its axial location before shielding and second to prevent the exposure of the needle after use. Though no forces are applied to the shield it is essential to maintain its position before shielding. The distal side of the latch 211 interacts with the housing slit 105 to prevent any displacement unless an axial force is applied when shielding is triggered.

The second function of the latch is to prevent the exposure of the needle after use. The discard latch 210 is shaped to make it relatively flexible for radial deflection yet highly rigid while axial force is applied. After shield 200 is moved to its shielded position the latch 210 leans on the housing 102 and prevents the shield from traveling back. Shield 200 also includes stoppers 212 to prevent any relative shield to housing rotational move and to prevent further axial move or disassembly of the shield.

Shield 200 is designed for injection molding. In particular the side walls of 210 and 212 could be parallel to the observation window 213 side walls. Features 213, 210 and 212 are design to match 110, 105 and 106. Flange 204 includes several local slits 216 on its inner side. These are intended to minimize the bulk of the shield.

Figure 19:
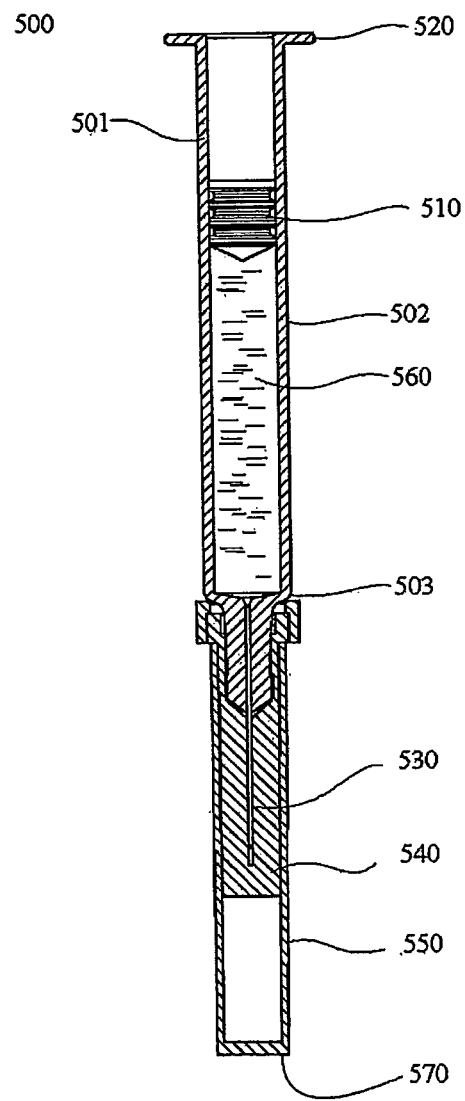
FIG. 19 Prefilled cartridge cross-section.

Cartridge assembly 500 is detailed in FIG. 19. Cartridge assembly includes the barrel 501 usually made of glass, a needle 530 attached to is distal end, and a flange 520 on its proximal end. The barrel 501 contains drug 560 retained in the barrel 501 by a stopper 510. The stopper is also used to push the drug through the cannula 530. The cannula 530 is covered by an elastomer sterility cover 540. The elastomer cover could be also covered by a plastic sterility cover 550. The 530 and 540 form a sterility cover assembly 570. The described components are common in conventional cartridges. The preferred embodiment in the invention is designed to integrate the standard components without any changes. Barrel 501 is sometimes covered by a laminate with a printed scale 502. Barrel 501 is a tube like part having a constant external diameter with the distal end 503 diameter decreasing towards the cannula. Spring 400 is a conventional coiled spring.

Assembly process description.

The safety syringe assembly process takes place in a clean environment with the filled cartridges reaching the final assembly as closed components with a sterile content. Additional aspect related to selection of materials will be discussed below.

Figure 20:
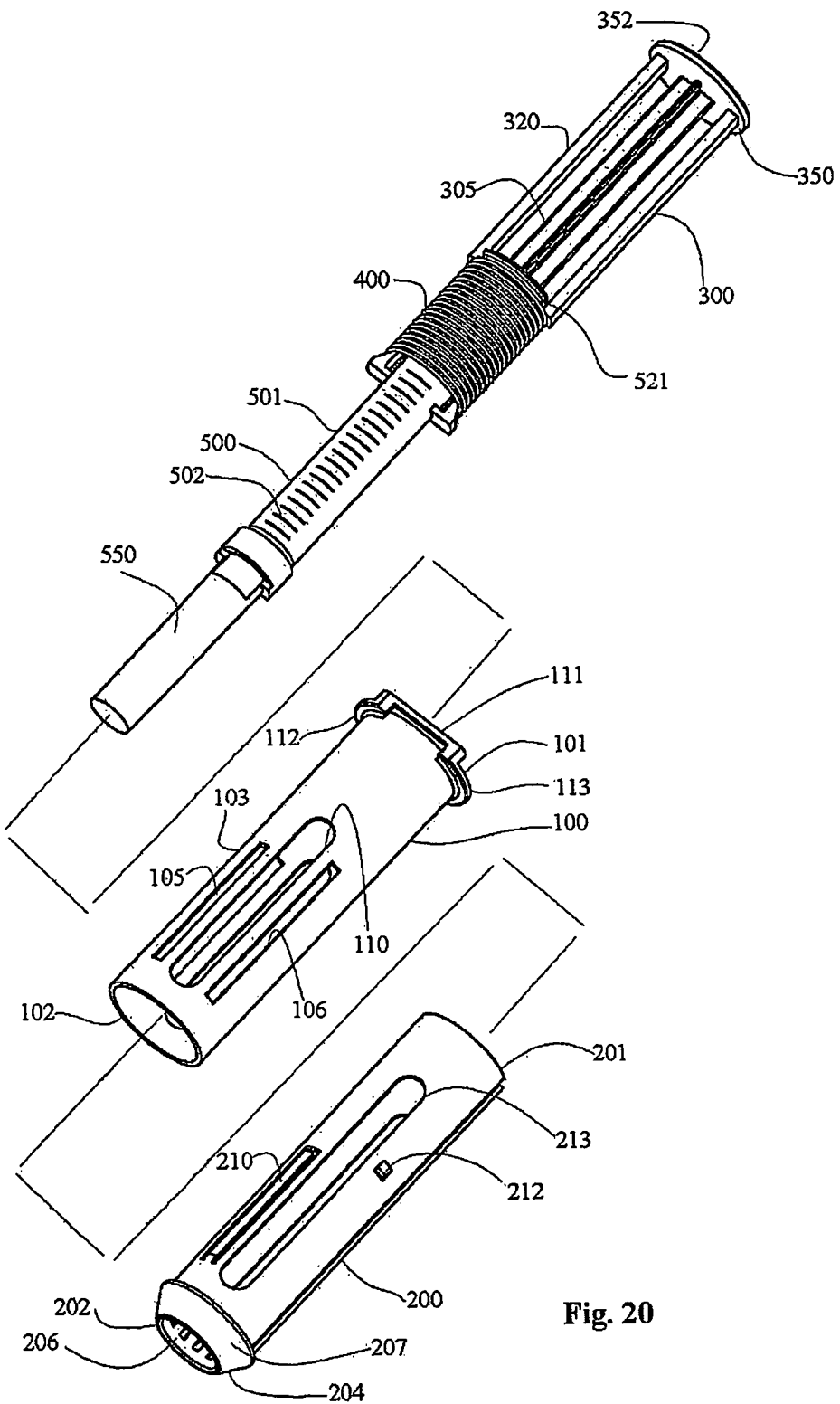
FIG. 20 Safety syringe exploded view.

One option of the assembly process is detailed below. An exploded view of the embodiment is shown in FIG. 20. The assembly starts with connecting the driver 300 to the cartridge 500 by either snapping or threading the element 345 to stopper 510. The position of the driver 300 relative to the flange 520 of the cartridge 500 should be controlled for a cartridge with a threaded stopper. A limited unthreading might be required for proper orientation of parts. Next step is the positioning of spring 400 on the front arm section 322. Spring 400 is placed on the driver and cartridge assembly by applying an axial force. Front taper 343 on the distal end of 320 supports the engagement with the spring. The spring 400 could be slightly deformed by a radial force to an oval shape to assist in the assembly.

Cartridge 500, driver 300 and preloaded spring 400 form a subassembly. This subassembly is inserted into proximal opening 115 of the housing 100. The rotational position it dictated is dictated by slits 114 guiding side arms 320. Spring 400 external diameter is smaller than the opening 115. The subassembly is moved forward until cartridge flange 520 is connected by snaps 111 to the housing 100. The connection is now permanent, no relative movement, axial or rotational between holder 100 and cartridge 500 is possible.

Final assembly step involves shield 200. Slits 214 are positioned to be engaged with arms 320. The external diameter of 203 fits to slide in the internal diameter of 103. The internal diameter of 203 is bigger than the external diameter of the spring 400. The shield 200 is inserted into the assembly from the distal end until the discard stopper 212 will contact the distal edge 102 of the housing 100. The proximal edge of 212 is tapered. An axial force applied to the shield 200 will deflect sections of the tubular body 203 separated by the cam guiding tracks 214. These will return to return to its original position once stoppers 212 will reach slits 106. This step completes the assembly.

Whilst the invention has been described above with reference to an injection device where the needle insertion and injection steps are carried out manually, the invention is also applicable to auto-injectors where one or both of these steps is carried our automatically. In particular, the shield driver means may additionally provide a driving force for said driver, with the coil spring being fixed at its proximal end to the housing, and the spring release mechanism fixing the spring to the driver at its distal end.

The invention claimed is:
1. An injection device comprising:
a housing having a proximate end and a distal end, the distal end having an opening therein;
a cartridge barrel within the housing, the cartridge barrel having proximate and distal ends;
a needle cannula fixed to the distal end of the cartridge barrel;
a stopper within the cartridge barrel;
a driver coupled to the stopper;

a shield coupled to the housing and slidable between a retracted and an extended position;

a spring activateable to urge the shield from the retracted position to the extended position; and at least one deformable side arm forming a portion of said driver and releasably retaining the spring in a compressed state, wherein the at least one side arm is biased into slidable contact with an exterior surface of said cartridge barrel and deflects radially inwardly at an end profile of the distal end of the cartridge barrel and, in turn, release the spring such that the spring slides past the at least one side arm and applies a force to the shield to urge the shield into the extended position.

2. An injection device according to claim 1, wherein the spring is a coil spring within which the cartridge barrel is located.

3. An injection device according to claim 2, wherein the driver further comprises a release mechanism for releasably fixing the spring relative to the driver in the compressed state, the release mechanism being actuatable by the side arms to release the spring.

4. An injection device according to claim 3, wherein the release mechanism comprises a catch provided on a radial outer surface of each deformable arm.

5. An injection device according to claim 1, wherein the at least one deformable arm is formed integrally with the driver.

6. An injection device according to claim 5, wherein each arm is naturally biased against the exterior surface of the cartridge barrel and arranged to follow the surface profile of the barrel.

7. An injection device according to claim 1, wherein said driver and said at least one side arm are a single molded plastic element.

8. The injection device of claim 1, wherein said driver is deformable during assembly.

9. An injection device comprising:
a housing having a proximate end and a distal end, the distal end having an opening therein;
a cartridge barrel within the housing, the cartridge barrel having proximate and distal ends;
a needle cannula fixed to the distal end of the cartridge barrel;
a stopper within the cartridge barrel;
a driver coupled to the stopper and arranged to be manually pushed through the housing;
a shield coupled to the housing and slidable between a retracted and an extended position;
a spring activateable to urge the shield from the retracted position to the extended position, wherein the driver carries the spring to a shield activation point; and
at least one deformable side arm forming a portion of said driver and being biased into slidable contact with an exterior surface of said cartridge barrel, said at least one side arm deflecting radially inwardly at an end profile of the distal end of the cartridge barrel, said deflecting triggering activation of the spring.

10. An injection device according to claim 9, wherein the spring is fixed at a proximal end thereof to the driver, and a spring release mechanism fixes the spring to the driver at a distal end thereof.

11. An injection device comprising:
a housing having a proximate end and a distal end, the distal end having an opening therein;
a cartridge barrel within the housing, the cartridge barrel having proximate and distal ends;
a needle cannula fixed to the distal end of the cartridge;
a stopper within the cartridge barrel;
a driver coupled to the stopper and;
a shield coupled to the housing and slidable between a retracted and an extended position;
a spring activateable to urge the shield from the retracted position to the extended position and additionally provides a driving force for said driver; and
at least one deformable side arm forming a portion of said driver and being biased into slidable contact with an exterior surface of said cartridge barrel, said at least one side arm deflecting radially inwardly at an end profile of the distal end of the cartridge barrel, said deflecting triggering activation of the spring.

12. An injection device according to claim 11, wherein the spring is fixed at a proximal end thereof to the driver, and a spring release mechanism fixes the spring to the driver at a distal end thereof.

13. An injection device comprising:
a cartridge barrel, said barrel arranged to contain a stopper and fluid therein and wherein said barrel has a distal first end and a second open end and a second end having a radial flange adjacent to the second end;
a needle cannula having a sharp distal end and a second open end, the fluid being in communication with said needle second end, and wherein said needle second end is coupled at said distal first end;
a housing surrounding said barrel, said housing having a distal open end adjacent the needle and a proximate end having a flange receiving the radial flange of the barrel;
a shield releasably retained by the housing, said housing and said shield arranged in a sliding relationship with the shield positioned primarily within the housing until release, wherein said shield includes radially deflectable latches;
a driver positioned partially within said housing, said driver equipped with at least one deformable side arm slidably disposed on an exterior surface of said barrel, said driver slidingly located within said housing for moving the stopper forward; and
a biasing spring adapted to bias the shield to a needle-shielded position to automatically cover the needle after said driver reaches the distal end of the barrel;
wherein the latches are configured to radially deflect and engage the distal end of the housing to retain the shield in the needle shielded position and prevent movement of the shield out of the needle-shielded position.

14. The injection device of claim 13, wherein the biasing spring is carried by the driver and is released to bias the shield when the end of said barrel is reached.

15. The injection device of claim 13, wherein the driver includes two cams configured to follow the exterior surface of the barrel to the distal end of the barrel.

16. The injection device of claim 13, wherein said latches prevent premature release of the shield.

* * * * *